United States Patent
Forster (10) Patent No.: US 10,678,382 B2
(45) Date of Patent: Jun. 9, 2020

(54) METHODS AND SYSTEMS FOR MONITORING MEDICATION COMPLIANCE

(71) Applicant: Avery Dennison Retail Information Services LLC, Mentor, OH (US)

(72) Inventor: Ian Forster, Essex (GB)

(73) Assignee: AVERY DENNISON RETAIL INFORMATION SERVICES, LLC, Mentor, OH (US)

( * ) Notice: Subject to any disclaimer, the term of this patent is extended or adjusted under 35 U.S.C. 154(b) by 475 days.

(21) Appl. No.: 14/584,090

(22) Filed: Dec. 29, 2014

(65) Prior Publication Data
US 2015/0302173 A1 Oct. 22, 2015

Related U.S. Application Data

(60) Provisional application No. 61/982,455, filed on Apr. 22, 2014.

(51) Int. Cl.
*G06F 3/044* (2006.01)
*G06F 19/00* (2018.01)
*G06F 3/0488* (2013.01)

(52) U.S. Cl.
CPC ............ *G06F 3/044* (2013.01); *G06F 3/0488* (2013.01); *G06F 19/3462* (2013.01)

(58) Field of Classification Search
CPC ..... G06F 3/044; G06F 3/0488; G06F 19/3462
See application file for complete search history.

(56) References Cited

U.S. PATENT DOCUMENTS

| 4,429,792 A | * | 2/1984 | Machbitz | ............. | B65D 75/327 |
| | | | | | 206/528 |
| 4,526,474 A | * | 7/1985 | Simon | ................... | A61J 7/0481 |
| | | | | | 116/308 |

(Continued)

FOREIGN PATENT DOCUMENTS

| CN | 202046575 | 9/2009 |
| EP | 1758050 | 2/2007 |

(Continued)

OTHER PUBLICATIONS

International Search Report and Written Opinion dated Mar. 11, 2016 for International Application No. PCT/US2015/064888 filed Dec. 10, 2015.

(Continued)

*Primary Examiner* — Nitin Patel
*Assistant Examiner* — Robert M Stone
(74) *Attorney, Agent, or Firm* — Avery Dennison Retail Information Services, LLC (57) ABSTRACT

Systems and methods are provided for monitoring medication compliance to allow a doctor or medical care provider to determine whether a subject is ingesting a prescribed medication at the proper times. This can include the capability of remote access to remotely monitor compliance. A medication container includes at least one medication-containing cell, with a cover overlaying the cell. An electronic device including a capacitive touchscreen is electrically coupled to the medication container and programmed to detect whether the cell has been accessed through the cover. The base of the cell may be in capacitive contact with the capacitive touchscreen or there may be an insulator therebetween. An adaptor may be provided to electrically couple the medication container and the electronic device.

15 Claims, 4 Drawing Sheets

(56) References Cited

U.S. PATENT DOCUMENTS

| | | | |
|---|---|---|---|
| 4,617,557 A * | 10/1986 | Gordon | A61J 7/04 206/531 |
| 4,660,991 A | 4/1987 | Simon | |
| 5,181,189 A * | 1/1993 | Hafner | A61J 7/0481 206/534 |
| 5,313,439 A | 5/1994 | Albeck | |
| 5,412,372 A * | 5/1995 | Parkhurst | G06F 19/3462 221/15 |
| 5,642,731 A * | 7/1997 | Kehr | A61J 7/0481 600/300 |
| 5,836,474 A * | 11/1998 | Wessberg | A61J 1/035 221/2 |
| 5,871,831 A * | 2/1999 | Zeiter | A61J 7/0481 206/524.1 |
| 5,905,653 A * | 5/1999 | Higham | G07F 17/0092 312/215 |
| 6,048,087 A * | 4/2000 | Laurent | A61J 7/0084 221/2 |
| 6,294,999 B1 * | 9/2001 | Yarin | A61J 7/0481 340/573.1 |
| 6,339,732 B1 * | 1/2002 | Phoon | A61J 7/0084 700/237 |
| 6,411,567 B1 * | 6/2002 | Niemiec | A61J 7/0481 368/10 |
| 6,664,887 B1 | 12/2003 | Fuchs | |
| 6,824,739 B1 | 11/2004 | Arney et al. | |
| 6,961,285 B2 * | 11/2005 | Niemiec | A61B 5/0002 206/531 |
| 6,973,371 B1 * | 12/2005 | Benouali | A61J 1/035 221/15 |
| 7,252,208 B1 | 8/2007 | Alvino et al. | |
| 7,298,343 B2 | 11/2007 | Forster et al. | |
| 7,828,147 B2 | 11/2010 | Caracciolo et al. | |
| 8,072,334 B2 | 12/2011 | Forster et al. | |
| 8,704,716 B2 | 4/2014 | Kato et al. | |
| 8,751,039 B1 | 6/2014 | Macoviak et al. | |
| 8,960,440 B1 | 2/2015 | Kronberg | |
| 9,172,130 B2 | 10/2015 | Forster | |
| 2001/0028308 A1 | 10/2001 | De La Huerga et al. | |
| 2002/0017996 A1 | 2/2002 | Niemiec et al. | |
| 2002/0111542 A1 * | 8/2002 | Warkentin | A61N 1/08 600/300 |
| 2003/0007421 A1 | 1/2003 | Niemiec et al. | |
| 2003/0046563 A1 | 3/2003 | Ma et al. | |
| 2003/0063524 A1 | 4/2003 | Niemiec et al. | |
| 2003/0111479 A1 | 6/2003 | Taneja et al. | |
| 2003/0121930 A1 | 7/2003 | Layer et al. | |
| 2004/0078879 A1 | 4/2004 | Zach et al. | |
| 2005/0062238 A1 * | 3/2005 | Broadfield | A61B 50/13 280/1 |
| 2005/0162255 A1 | 7/2005 | Goel et al. | |
| 2005/0162979 A1 * | 7/2005 | Ostergaard | A61J 1/035 368/10 |
| 2005/0237222 A1 * | 10/2005 | Bogash | A61J 1/035 340/870.07 |
| 2005/0241983 A1 * | 11/2005 | Snyder | A61J 7/0481 206/539 |
| 2005/0256830 A1 | 11/2005 | Siegel et al. | |
| 2006/0061472 A1 * | 3/2006 | Lovoi | A61J 3/007 340/572.1 |
| 2006/0071774 A1 * | 4/2006 | Brown | G06Q 10/087 340/522 |
| 2006/0079996 A1 | 4/2006 | Benouali | |
| 2006/0124656 A1 * | 6/2006 | Popovich, Jr. | G07F 9/026 221/9 |
| 2006/0144749 A1 | 7/2006 | Arnold et al. | |
| 2006/0202830 A1 | 9/2006 | Scharfeld et al. | |
| 2007/0018819 A1 | 1/2007 | Streeb et al. | |
| 2007/0023316 A1 * | 2/2007 | Coe | A61J 1/03 206/534 |
| 2007/0246396 A1 | 10/2007 | Brollier | |
| 2008/0012579 A1 * | 1/2008 | Kuhns | G06K 19/0717 324/652 |
| 2008/0223936 A1 | 9/2008 | Mickle et al. | |
| 2009/0210247 A1 | 8/2009 | Chudy et al. | |
| 2009/0218846 A1 | 9/2009 | Nguyen et al. | |
| 2009/0278626 A1 | 11/2009 | Lee | |
| 2009/0278688 A1 | 11/2009 | Tuttle | |
| 2009/0294521 A1 | 12/2009 | De La Huerga et al. | |
| 2009/0309704 A1 | 12/2009 | Chang et al. | |
| 2010/0089791 A1 * | 4/2010 | Rosenbaum | A61J 1/035 206/531 |
| 2010/0114367 A1 * | 5/2010 | Barrett | G06F 19/3456 700/236 |
| 2010/0187243 A1 | 7/2010 | Layer et al. | |
| 2010/0314282 A1 | 12/2010 | Bowers | |
| 2011/0037485 A1 | 2/2011 | Kiy | |
| 2012/0003928 A1 * | 1/2012 | Geboers | A61J 7/0084 455/41.1 |
| 2012/0109397 A1 | 5/2012 | Shim et al. | |
| 2012/0125994 A1 | 5/2012 | Heath et al. | |
| 2012/0228192 A1 | 9/2012 | Niven | |
| 2012/0229279 A1 * | 9/2012 | Conley | G06Q 10/087 340/568.1 |
| 2013/0044007 A1 | 2/2013 | Paavilainen et al. | |
| 2013/0195326 A1 | 8/2013 | Bear et al. | |
| 2013/0222135 A1 * | 8/2013 | Stein | A61J 7/0409 340/540 |
| 2013/0285681 A1 | 10/2013 | Wilson et al. | |
| 2014/0039445 A1 | 2/2014 | Austin et al. | |
| 2014/0048442 A1 | 2/2014 | Maijala et al. | |
| 2014/0052467 A1 * | 2/2014 | Maijala | A61J 1/035 705/2 |
| 2014/0166529 A1 * | 6/2014 | Fung | A61J 1/03 206/534 |
| 2014/0243749 A1 * | 8/2014 | Edwards | A61M 5/31 604/187 |
| 2014/0262918 A1 | 9/2014 | Chu | |
| 2014/0288942 A1 * | 9/2014 | Blochet | A61J 7/04 705/2 |
| 2014/0340198 A1 | 11/2014 | Kawase et al. | |
| 2014/0354433 A1 | 12/2014 | Buco et al. | |
| 2014/0360898 A1 * | 12/2014 | Kantor | A45C 11/00 206/216 |
| 2015/0048100 A1 | 2/2015 | Dickie et al. | |
| 2015/0048102 A1 * | 2/2015 | Dickie | A61J 1/03 221/2 |
| 2015/0048170 A1 | 2/2015 | Forster | |
| 2015/0274402 A1 | 10/2015 | Elliott | |
| 2015/0283036 A1 * | 10/2015 | Aggarwal | A61J 7/04 206/534 |
| 2015/0286852 A1 | 10/2015 | Sengstaken, Jr. | |
| 2015/0325336 A1 | 11/2015 | Maples | |
| 2015/0339566 A1 | 11/2015 | Forster | |
| 2015/0347712 A1 | 12/2015 | Flori et al. | |
| 2015/0347713 A1 | 12/2015 | Seeger | |
| 2015/0356845 A1 | 12/2015 | Forster | |
| 2016/0019452 A1 | 1/2016 | Forster | |
| 2016/0106622 A1 * | 4/2016 | Van De Wouw | A61J 1/03 206/534 |
| 2016/0132661 A1 | 5/2016 | Dixit et al. | |
| 2016/0137380 A1 | 5/2016 | Kosaka | |
| 2016/0143807 A1 | 5/2016 | Ika et al. | |
| 2016/0143809 A1 * | 5/2016 | Webster | A61J 1/035 206/531 |
| 2016/0147976 A1 | 5/2016 | Jain | |
| 2016/0158108 A1 | 6/2016 | Gofer et al. | |
| 2016/0158109 A1 * | 6/2016 | Nova | G06F 19/3462 206/534 |
| 2016/0367435 A1 | 12/2016 | Ahmadi | |
| 2017/0011240 A1 | 1/2017 | Forster | |
| 2017/0053095 A1 | 2/2017 | Blum et al. | |
| 2017/0165151 A1 | 6/2017 | Schmid et al. | |
| 2017/0337157 A1 | 11/2017 | Rothschild | |
| 2018/0012117 A1 | 1/2018 | Forster | |
| 2018/0042105 A1 | 2/2018 | Anderson | |
| 2018/0156756 A1 | 6/2018 | Forster | |
| 2018/0319519 A1 | 11/2018 | Stange et al. | |

(56) References Cited

U.S. PATENT DOCUMENTS

FOREIGN PATENT DOCUMENTS

| EP | 2026253 | 2/2009 |
| WO | 2006002667 | 1/2006 |
| WO | 2008000279 | 1/2008 |
| WO | 2009116108 | 9/2009 |

OTHER PUBLICATIONS

International Search Report and Written Opinion dated Dec. 5, 2016 for International Application No. PCT/US2016/039714 filed Jun. 28, 2016.
International Search Report and Written Opinion dated Oct. 4, 2016 for International Application No. PCT/US2016/039720 filed Jun. 28, 2016.
International Search Report dated Sep. 29, 2015 for International Application No. PCT/US2015/038763 filed Jul. 1, 2015.
International Preliminary Report on Patentability and Written Opinion dated Jan. 10, 2017 for International Application No. PCT/US2015/038763 filed Jul. 1, 2015.
International Preliminary Report on Patentability dated Jun. 13, 2017 for International Application No. PCT/US2015/064888 filed Dec. 10, 2015.
International Search Report and Written Opinion dated Sep. 28, 2017 for International Application No. PCT/US2017/041125 filed Jul. 7, 2017.
International Preliminary Report on Patentability dated Jan. 8, 2019 for International Application No. PCT/US2017/041125 filed Jul. 1, 2017.

* cited by examiner

METHODS AND SYSTEMS FOR MONITORING MEDICATION COMPLIANCE

CROSS-REFERENCE TO RELATED APPLICATION(S)

The present application claims priority from U.S. Provisional Application No. 61/982,455 filed Apr. 22, 2014 which is incorporated by herein by reference in its entirety.

BACKGROUND

Field of the Disclosure

The present subject matter relates to monitoring the medication intake of a subject. More particularly, the present subject matter relates to monitoring the medication intake of a subject using the combination of a medication container and an electronic device with a capacitive touchscreen.

Description of Related Art

Frequently, a doctor or medical care provider will issue instructions to a subject to periodically ingest one or more doses of medication in the form of a pill or tablet or capsule or the like as part of a treatment regimen. Unless the subject is within a facility under the control of the doctor or medical care provider (e.g., a hospital or nursing home), it can be difficult for the doctor or medical care provider to know whether the subject is ingesting the prescribed medication at the proper times. Accordingly, it would be advantageous to provide systems and methods that allow a doctor or medical care provider to monitor the medication compliance of a subject.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as may be set forth in the claims appended hereto.

In one aspect, a system for remotely monitoring medication compliance includes a medication container and an electronic device including a capacitive touchscreen electrically coupled to the medication container. The medication container includes at least one medication-containing cell, with a cover overlaying the cell, and the electronic device is programmed to detect whether the cell has been accessed through the cover.

In another aspect, an adaptor is provided for electrically coupling a medication container and an electronic device having a capacitive touchscreen. The adaptor includes a first portion and a second portion. The first portion is configured to receive at least a portion of a medication container of the type including at least one medication-containing cell. The second portion is configured to be placed adjacent to a capacitive touchscreen of an electronic device. A conductor extends between the first and second portions of the adaptor and is configured to electrically couple the cell of the medication container and the capacitive touchscreen for detecting whether medication has been removed from the cell.

In yet another aspect, a method of monitoring medication compliance includes providing a medication container including at least one medication-containing cell, with a cover overlaying the cell. An electronic device including a capacitive touchscreen is also provided, and the capacitive touchscreen is electrically associated with the medication container. The capacitive touchscreen is then used to detect whether the cell has been accessed through the cover.

DESCRIPTION OF THE ILLUSTRATED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 1:
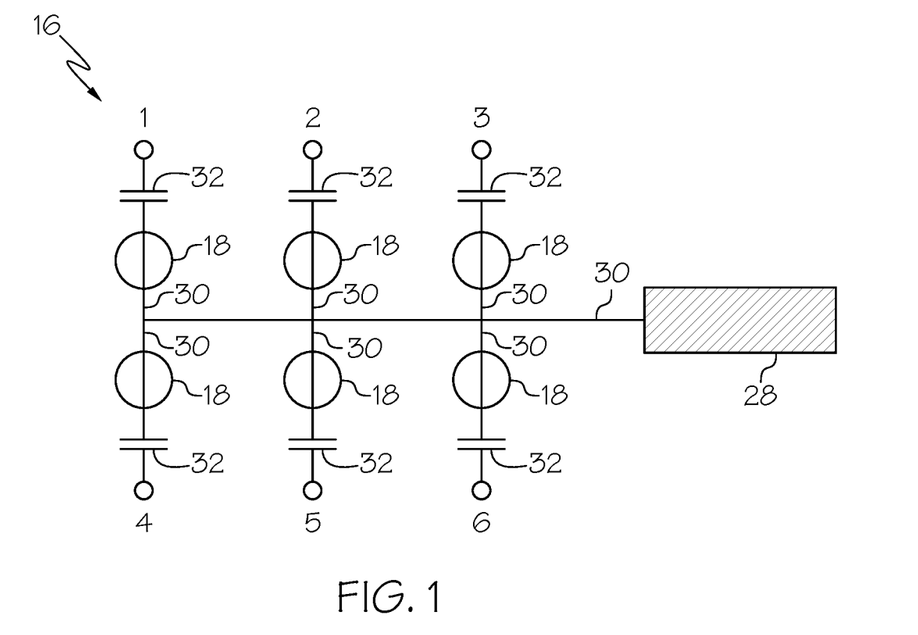
FIG. 1 is a diagrammatic view of a circuit for electrically coupling a medication container to an electronic device having a capacitive touchscreen according to an aspect of the present disclosure.
Figure 7:
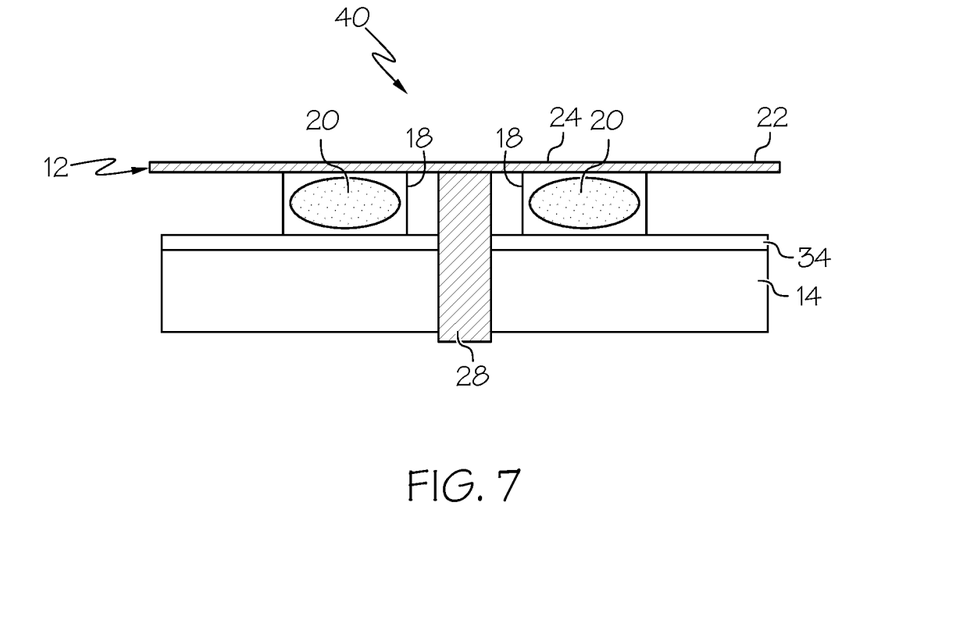
FIG. 7 is a side elevational view of another embodiment of a system in which a medication container and an electronic device having a capacitive touchscreen are electrically coupled to monitor medication compliance.
Figure 8:
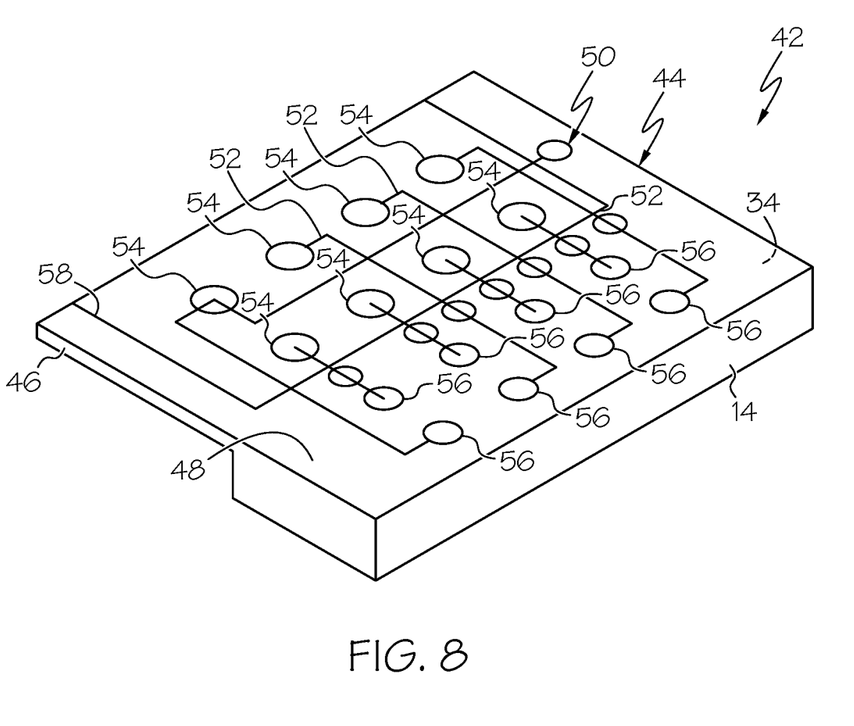
FIG. 8 is a perspective view of a system in which a medication container and an electronic device having a capacitive touchscreen are electrically coupled using an adapter to monitor medication compliance.

According to an aspect of the present disclosure, a doctor or medical care provider may remotely monitor medication compliance through the use of a system 10 which combines a medication container 12 and an electronic device 14. FIG. 1 illustrates an exemplary circuit 16 by which the status of a medication-containing cell 18 of a medication container 12 may be monitored using an electronic device 14 that is electronically coupled to the medication container. FIGS. 2-6 illustrate one embodiment of such a system 10, while FIGS. 7 and 8 illustrate two alternative embodiments of such a system.

In the embodiment of FIGS. 1-6, a medication container 12 includes at least one cell 18 in which a medication 20 is contained. Preferably, the medication container 12 includes a plurality of identical cells 18, but it is also within the scope of the present disclosure for a medication container to include differently configured cells or only one cell.

Each cell 18 may be formed of any suitable material but, in one embodiment, each cell is formed of a plastic material or another material that is substantially non-conductive. It may be advantageous for the cells 18 to be formed of a material that is generally rigid, but sufficiently deformable that a human may deform the individual cells using a finger or digital force and manipulation. In a preferred embodiment, the body of the medical container 12 takes the general form of a blister pack, with a thin plastic sheet 22 (FIGS. 2 and 3) being provided with a plurality of vacuum-formed depressions or formations that each defines a cell 18 for receiving a dose of medication 20. While it may be preferred for a medication container having a plurality of cells to be provided with a single plastic sheet that is formed to define all of the cells, it is also within the scope of the present disclosure for the cells of a single medication container to be separately or non-integrally formed.

Figure 2:
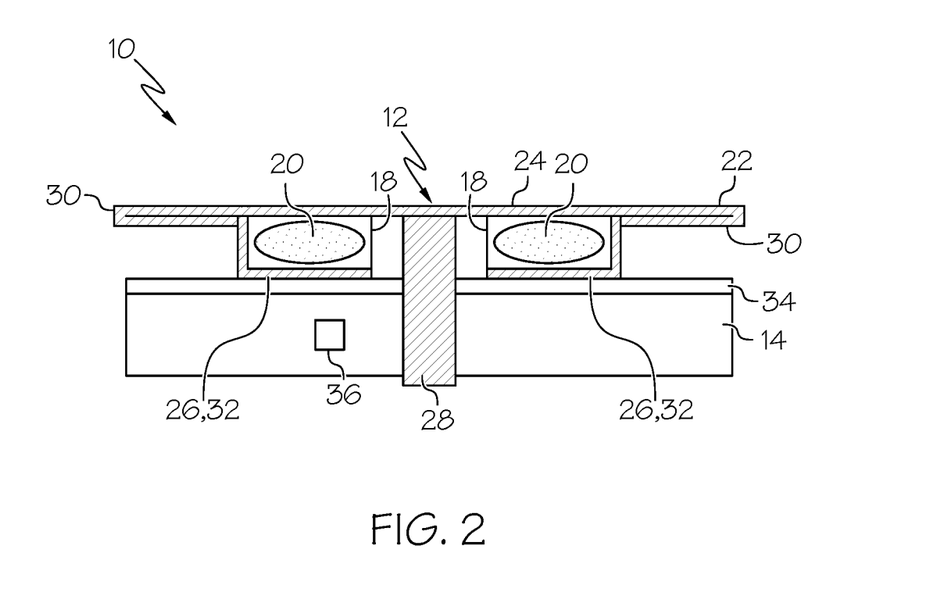
FIG. 2 is a side elevational view of a system in which a medication container and an electronic device having a capacitive touchscreen are electrically coupled to monitor medication compliance.
Figure 3:
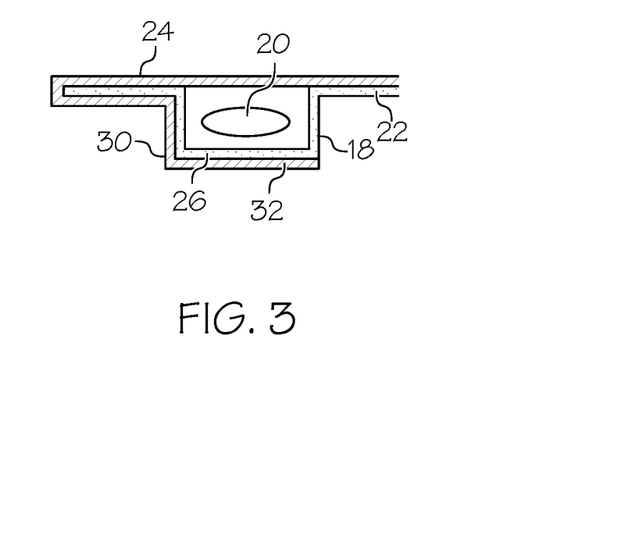
FIG. 3 is a detail view of a medication-containing cell of the medication container of FIG. 2.
Figure 4:
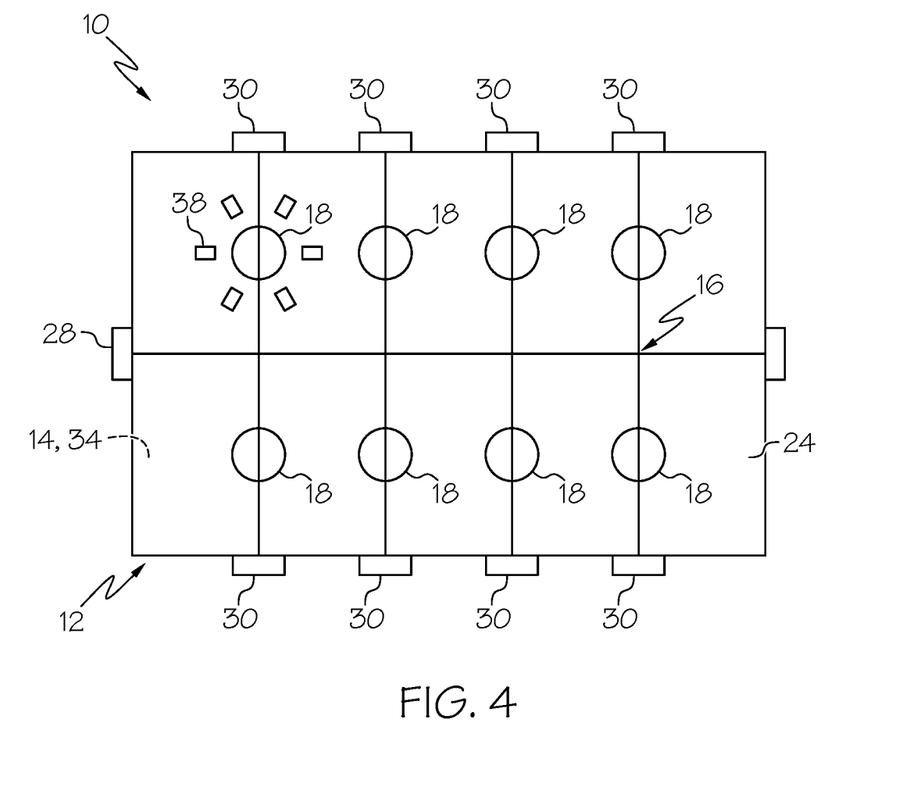
FIG. 4 is a top plan view of the system of FIG. 2.

Each cell 18 is closed or overlaid by a cover 24 through which medication 20 within the cell 18 may be accessed. In one embodiment, the cover 24 is a thin sheet of material, such as a metallic foil or an at least partially light-transmissive (e.g., transparent or translucent) sheet, which may be broken to allow a medication 20 to pass out of the cell 18. In such an embodiment, a base 26 of the cell 18 may be pressed toward the frangible cover 24 by a user until the force on the cover 24 exceeds the strength of the cover 24, at which point the cover 24 breaks and the medication 20 may be removed from the cell 18. Alternatively, the cell 18 may remain untouched, while the cover 24 is directly engaged and broken to remove medication 20 from the cell 18. If the medication container 12 is provided with a plurality of cells 18, it may be preferred for a single cover 24 to overlay all of the cells 18, but it is also within the scope of the present disclosure for two or more cells of the same medication container to be provided with separate covers. For example, in one embodiment, different cells are each overlaid by separate, non-frangible (e.g., hinged) covers.

In the embodiment of FIGS. 1-6, a circuit 16 is incorporated into the medication container 12. The circuit 16 of FIG. 1 includes a tab or conductor 28 that provides a virtual ground, as will be described in greater detail herein. A conductor 30 associated with the cover 24 extends from the tab 28 to cross over the cell 18. If the medication container 12 is provided with a plurality of cells 18, as in the illustrated embodiment, a single conductor 30 may be configured to cross over each of the cells 18, but it is also within the scope of the present disclosure for separate cells to have separate conductors associated therewith. In a particular embodiment, the conductor 30 may be printed onto the cover 24 or otherwise integrated into the cover 24, but it also within the scope of the present disclosure for the conductor to be separately provided from the cover.

The illustrated circuit 16 further includes a capacitor 32 that is electrically coupled to the tab 28 by the conductor 30, with the portion of the conductor 30 passing over the cell 18 positioned between the tab 28 and the capacitor 32. In the illustrated embodiment, the tab 28 is associated with the same surface of the medication container 12 as the cover 24, which is opposite the surface of the medication container 12 where the bases 26 of the cells 18 are located. In the orientation of FIG. 2, the upper surface of the medication container 12 is shown as being associated with the cover 24, while the cells 18 extend downwardly from the lower surface of the medication container 12. In the illustrated embodiment, the conductor 30 is wrapped around the edge of the medication container 12 to place the capacitor 32 on the lower surface, preferably directly below the cell 18. As best shown in FIG. 2, so positioning the capacitor 32 at the base 26 of the cell 18 places it into contact with the capacitive touchscreen 34 of an associated electronic device 14, thereby creating a virtual touch point, when the medication container 12 is mounted onto the electronic device 14, as will be described in greater detail herein.

The electronic device 14 of the system 10 may be variously configured, provided that it includes a capacitive touchscreen 34. For example, the electronic device 14 may be a mobile phone or a tablet computer or a controller of an electronic gaming device or the like. Preferably, the capacitive touchscreen 34 is of the type that may detect multiple touch points simultaneously in order to accommodate a medication container 12 with a plurality of cells 18, as in the illustrated embodiment.

Figure 5:
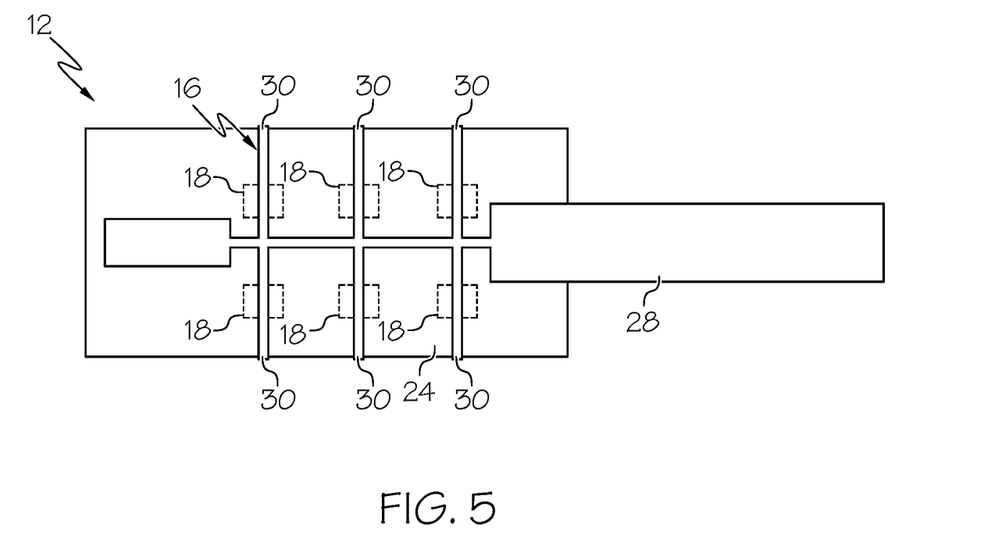
FIG. 5 is a top plan view of the medication container of FIG. 2.
Figure 6:
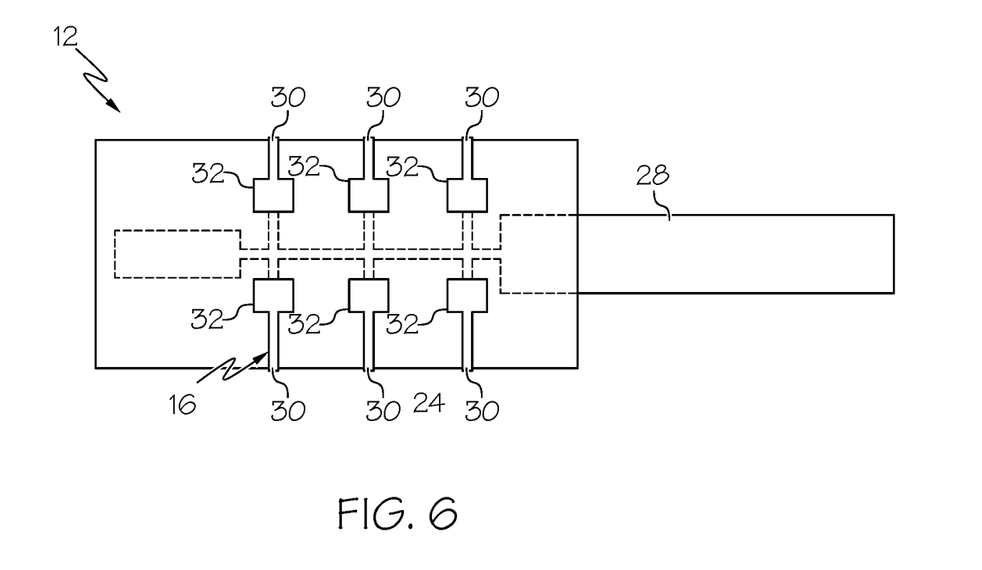
FIG. 6 is a bottom plan view of the medication container of FIG. 2.

In use, a medication container 12 having a circuit 16 of the type shown in FIG. 1 is provided, as in FIGS. 5 and 6. The medication container 12 is connected to the electronic device 14 so as to place the base 26 of the cell or cells 18 against the capacitive touchscreen 34 (FIG. 2) of the electronic device 14, thereby bringing the capacitor or capacitors 32 of the circuit 16 into contact with the capacitive touchscreen 34, creating one or more virtual touch points. The tab 28 of the circuit 16 may be at least partially wrapped around the edge of the electronic device 14 to contact an insulated portion thereof (FIG. 2), creating a virtual ground for the circuit 16. Additional means may also be provided for securing the medication container 12 to the electronic device 14, as need be. Alternatively, in one embodiment, the tab 28 may be the sole means by which the medication container 12 is connected to the electronic device 14, with the tab 28 being sufficiently flexible to define a hinge that allows the medication container 12 to be temporarily swung or pivoted away from the capacitive touchscreen 34 for accessing the medication 20, before swinging or pivoting the medication container 12 back into position against the capacitive touchscreen 34.

With the circuit 16 of the medication container 12 creating at least one touch point on the capacitive touchscreen 34, the electronic device 14 is effectively electrically coupled to the medication container 12. As such, the electronic device 14 is able to detect the presence of the cell 18 and register it as containing a medication 20, with the cover 24 intact over the cell 18. In one embodiment, the electronic device 14 may be programmed to continuously monitor the status of the cell or cells 18. In another embodiment, the electronic device 14 may include an accelerometer 36 and may be programmed to monitor the status of the cell or cells 18 only when the accelerometer 36 detects movement of the electronic device 14 (e.g., when a subject picks up the system 10 to remove medication 20 from a cell 18).

Accessing a cell 18 through the cover 24 to remove the medication 20 disrupts the circuit 16 at the location of the cell 18, for example by severing or breaking the conductor 30 at the cell 18. By so changing the structure of the circuit 16, the signal being received by the electronic device 14 from the cell 18 via the capacitive touchscreen 34 will change. The electronic device 14 may be programmed to register such a change in (or absence of) the signal being received by the capacitive screen 34 at the touch point corresponding to the location of the cell 18 as an indication that the medication 20 has been removed from the cell 18. If the medication container 12 includes a plurality of cells 18, the electronic device 14 may separately monitor the status of each cell 18 and distinguish them based on their different locations with respect to the capacitive touchscreen 34. This may be especially advantageous if the various cells contain different medications that are to be ingested by the subject at particular times.

The electronic device 14 may be programmed to respond to the change at the touch point in any of a number of ways. For example, it may send a signal to the doctor or medical care provider to indicate that a particular medication was taken by the subject at a particular date and time. In another embodiment, the electronic device 14 may store information about the event in an internal database or in an external storage location, which may be later accessed by the doctor or medical care provider.

In addition to responding to a change at a virtual touch point, the electronic device 14 may be programmed to execute any of a number of other operations in connection with medication monitoring. For example, if the medication container 12 is at least partially light-transmissive, then the electronic device 14 may be programmed to display one or more visual indications 38 (FIG. 4) adjacent to a cell 18 to alert the subject that it is time to access the cell 18 and ingest the medication 20 contained therein or to perform some other action. Alternatively, if the medication container 12 and/or cover 24 are formed of a substantially opaque material, the medication container 12 and/or cover 24 may include voids or apertures through which the underlying capacitive touchscreen 34 may be seen in order to allow the electronic device 14 to visually alert the subject. Additionally, or alternatively, the electronic device 14 may be programmed to emit an alarm or other audible signal (such as recorded speech) and/or vibrate to alert the subject that it is time to take a dose of medication. The electronic device 14 may also be programmed to provide the subject with a direct voice link to the doctor or medical care provider (either initiated by the doctor/medical care provider to offer guidance or by the subject to request assistance) when accessing the medication 20.

In an alternative embodiment, which is shown in FIG. 7, a different mechanism is used to ascertain whether a cell 18 has been accessed through the cover 24 of the medication container 12 to remove the medication 20. In particular, the dielectric constant "k" of the medication 20 differs from that of the cover 24 (particularly, the circuit incorporated into the cover 24), such that there is a localized difference in capacitance at the location of a cell 18 containing a dose of medication 20. For example, in one embodiment, calcium carbonate has a dielectric constant of 9.1, which causes a localized increase in the capacitance at the location of the associated cell 18. When the cell 18 is accessed through the cover 24 and the medication 20 is removed, the capacitance at the cell 18 will change (decrease in the case of calcium carbonate), which changes the signal received by the electronic device 14. The electronic device 14 may be programmed to recognize a change in the localized capacitance as an indication that the medication 20 has been removed from the cell 18 positioned at the location of the changed capacitance. As in the embodiment, of FIGS. 2-6, the system 40 of FIG. 7 may be configured to accommodate several cells 18, with the electronic device 14 being programmed to monitor the status of all of the cells 18 and pinpoint which particular cell has been accessed through the cover 24 by a subject.

For some subjects, a system in which the cells of the medication container are positioned at a location that is offset from the capacitive touchscreen may be preferred to a system in which the cells are positioned in contact with the capacitive touchscreen and accessed with the cells in that position or after temporarily moving the medication container out of contact with the capacitive touchscreen. Subjects may also prefer a system in which a standard medication container, rather than a medication container of the type described herein with an incorporated circuit, is used in combination with an electronic device. To that end, another embodiment of a system 42 according to the present disclosure may include an adaptor or case 44 that electrically couples a standard medication container to an electronic device 14 having a capacitive touchscreen 14 (FIG. 8).

In the illustrated embodiment, the adaptor 44 has a first portion 46 that is positioned laterally or otherwise offset from a second portion 48 of the adaptor 44. The first portion 46 is configured to receive at least a portion of a medication container having one or more medication-containing cells, while the second portion 48 is configured to be placed adjacent to the capacitive touchscreen 34 of an electronic device 14. The adaptor 44 includes a circuit 50 with one or more conductors 52 extending between the first portion 46 and the second portion 48. For each cell of the medication container, the first portion 46 of the adaptor 44 may include a corresponding cell connection point 54, with a conductor 50 extending between the cell connection point 54 and a corresponding touchscreen connection point 56 at the second portion 48 of the adaptor 44.

When the second portion 48 of the adaptor 44 is secured or connected to the electronic device 14, each touchscreen connection point 56 engages the capacitive touchscreen 34 of the electronic device. When a medication container is associated with the first portion 46 of the adaptor 44, such as by sliding the medication container into a slot 58 defined in the first portion 46, each cell will be positioned at a corresponding cell connection point 54. On account of the conductor 52 extending between each cell connection point 54 and the corresponding touchscreen connection point 56, connecting both the medication container and the electronic device 14 to the adaptor 44 electrically couples each cell of the medication container to a corresponding location of capacitive touchscreen 34, creating one or more virtual touch points on the capacitive touchscreen 34. With both the medication container and the electronic device 14 connected to the adaptor 44, the system 42 may be used to detect whether a cell of the medication container has been accessed through the cover of the medication container according to the principles described above with respect to the embodiments of FIGS. 1-6 and 7.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A system for monitoring medication compliance, comprising:
   a medication container including at least one medication-containing cell, with a cover overlaying the cell, such that the cell includes a medication having a dielectric constant that differs from a dielectric constant of the cover; and
   a capacitor that is coupled to a tab which is coupled to the cover; and
   an electronic device including a capacitive touchscreen electrically coupled to the medication container, wherein the electronic device is programmed to detect whether the cell has been accessed through the cover and the electronic device is further programmed to transmit a signal when the cell has been accessed through the cover and the cell includes a base in capacitive contact with the capacitive touchscreen; and where the device is programmed to provide a direct voice link.

2. The system of claim 1, wherein the cover comprises a frangible foil material that is configured to be broken to access the cell.

3. The system of claim 1, wherein
the medication container includes a plurality of cells;
the cells are positioned at different locations with respect to the capacitive touchscreen,
the cover overlays each of the cells, and
the electronic device is further programmed to detect for each cell the location of said cell and whether said cell has been accessed through the cover.

4. The system of claim 1, wherein the electronic device is further programmed to continuously monitor the status of the cell.

5. The system of claim 1, wherein the electronic device includes an accelerometer and is programmed to monitor the status of the cell only when the accelerometer detects movement of the electronic device.

6. The system of claim 1, further comprising an adaptor configured to receive at least a portion of the medication container, with the cell positioned at a location offset from the capacitive touchscreen, wherein the adaptor electrically couples the cell to the capacitive touchscreen.

7. The system of claim 1, wherein a conductor is electrically coupled to the cover and in contact with an insulated portion of the electronic device to provide a virtual ground.

8. The system of claim 1, wherein the medication container includes a conductor pattern formed on an at least partially light-transmissive material.

9. The system of claim 8, wherein the electronic device is further programmed to display one or more visual indications on the capacitive touchscreen to indicate that the cell is to be accessed through the cover.

10. An adaptor for electrically coupling a medication container and an electronic device having a capacitive touchscreen, comprising:
a first portion configured to receive at least a portion of a medication container of the type including at least one medication-containing cell that includes a base in capacitive contact with the capacitive touchscreen, a cover, and a medication having a dielectric constant that differs from a dielectric constant of the cover; and
a capacitor that is coupled to a tab, where the tab is at least partially wrapped around an edge of the electronic device; and
a second portion configured to be placed adjacent to a capacitive touchscreen of an electronic device; and
a conductor extending between the first portion and the second portion and configured to electrically couple the cell of the medication container and the capacitive touchscreen for detecting whether medication has been removed from the cell such that the first portion is configured to receive at least a portion of a medication container of the type including a plurality of cells, and further comprising a plurality of conductors extending between the first portion and the second portion, with each conductor being configured to electrically couple at least one of the plurality of cells of the medication container and the capacitive touchscreen.

11. The adaptor of claim 10, wherein the first portion is configured to position the cell of the medication container at a location offset from the capacitive touchscreen.

12. A method of monitoring medication compliance, comprising:
providing a medication container including at least one medication-containing cell, with a cover overlaying the cell, such that the cell includes a medication having a dielectric constant that differs from a dielectric constant of the cover, where the medication container includes a flexible tab;
providing an electronic device including a capacitive touchscreen;
electrically associating the capacitive touchscreen and the medication container via a base associated with at least one cell in capacitive contact with the capacitive touchscreen;
detecting whether the cell has been accessed through the cover using the capacitive touchscreen; and
transmitting a signal using the electronic device when the cell has been accessed through the cover; and where the electronic device is programmed to vibrate.

13. The method of claim 12, further comprising displaying one or more visual indications on the capacitive touchscreen to indicate that the cell is to be accessed through the cover.

14. The method of claim 12, further comprising continuously monitoring the status of the cell.

15. The method of claim 12, further comprising detecting movement of the electronic device and monitoring the status of the cell only when the electronic device is in motion.

* * * * *